US008543345B1

(12) United States Patent
Henry

(10) Patent No.: US 8,543,345 B1
(45) Date of Patent: Sep. 24, 2013

(54) ELECTROCHEMICAL POTENTIOSTAT EMPLOYING SMART ELECTRODES

(75) Inventor: Kent Douglas Henry, Laramie, WY (US)

(73) Assignee: ADA Technologies, Inc., Littleton, CO (US)

( * ) Notice: Subject to any disclaimer, the term of this patent is extended or adjusted under 35 U.S.C. 154(b) by 647 days.

(21) Appl. No.: 12/535,585

(22) Filed: Aug. 4, 2009

Related U.S. Application Data

(60) Provisional application No. 61/086,013, filed on Aug. 4, 2008.

(51) Int. Cl.
*G01R 5/32* (2006.01)
*G01R 5/28* (2006.01)
*G01R 5/34* (2006.01)
*G06F 3/00* (2006.01)

(52) U.S. Cl.
USPC .................. 702/64; 702/57; 702/65; 702/186

(58) Field of Classification Search
USPC ............. 702/19, 23, 25, 64, 65, 85, 104, 190; 73/19.1; 204/412; 205/775; 324/700
See application file for complete search history.

(56) References Cited

U.S. PATENT DOCUMENTS

| 5,526,287 A | * | 6/1996 | French | 702/104 |
| 5,839,094 A | * | 11/1998 | French | 702/91 |
| 6,908,536 B2 | * | 6/2005 | Beckmann | 204/412 |
| 7,007,541 B2 | * | 3/2006 | Henry et al. | 73/19.1 |
| 7,090,764 B2 | * | 8/2006 | Iyengar et al. | 205/775 |
| 7,180,309 B1 | * | 2/2007 | Yang | 324/700 |

OTHER PUBLICATIONS

Background for the above captioned application (previously provided).

* cited by examiner

*Primary Examiner* — Marc Armand
*Assistant Examiner* — Felix Suarez
(74) *Attorney, Agent, or Firm* — Sheridan Ross PC

(57) ABSTRACT

The present invention is directed to an electrochemical tool consisting of a potentiostat and user replaceable sensors and/or electrodes accompanied by an electronic memory that contains information that directs the potentiostat operation. The potentiostat is designed to operate with sensors employing a user customizable sensor and/or electrode memory. The customizable memory allows storing of information from a user and/or manufacturer related to a unique sensor identifier, calibration information, and/or an operational sequence to be employed by the potentiostat to properly operate the sensor and/or electrodes. A further aspect is to provide an electrode with pre-programmed electrode attributes.

20 Claims, 8 Drawing Sheets

ELECTROCHEMICAL POTENTIOSTAT EMPLOYING SMART ELECTRODES

CROSS REFERENCE TO RELATED APPLICATION

The present application claims the benefits of U.S. Provisional Application Ser. No. 61/086,013, filed Aug. 4, 2008, having the same title, which is incorporated herein by this reference in its entirety.

FIELD

The invention relates generally to electrochemical electrodes and/or sensors and particularly to intelligent electrochemical electrodes and/or sensors.

BACKGROUND

Electrochemical sensors are used to determine the concentrations and identities of various analytes in samples such as fluids and dissolved solid materials. Electrochemical sensors are used in a wide variety of applications, including chemical and biochemical science, occupational safety, medical engineering, process measuring engineering, and environmental analysis. By way of illustration, electrochemical gas sensors are well known for detecting and quantifying toxic gases such as carbon monoxide, hydrogen sulfide, nitrogen oxides, chlorine, sulfur dioxide and the like. Electrochemical aqueous analyte sensors are well known for detecting and quantifying analytes such as hydronium, dissolved oxygen, and halides.

A typical electrochemical sensor has a plurality of electrodes, including two, three, and four or more electrodes. Commonly, an electrochemical sensor includes an auxiliary electrode, reference electrode, and one or more working electrodes. The electrodes are typically fabricated from electrically conductive solid materials, thin films, and liquids. The working electrode provides the surface where the target electrochemical reactions take place. The electrodes are typically arranged in an inert, non-electrically conductive housing which contains sealed electrical contacts to connect the electrodes to an electrochemical controller such as a potentiostat.

The electrodes of an electrochemical sensor provide a surface at which an oxidation or a reduction reaction occurs. The ionic conduction of the analyte solution in contact with the electrode is coupled with the electron conduction of the working and auxiliary electrodes to provide a complete circuit for a current. The reference electrode, such as a silver/silver chloride electrode, provides a reference voltage. As will be appreciated, the auxiliary electrode is typically made of a material having a low work function and has significantly greater surface area than the working electrode. In a typical electrochemical sensor, the analyte to be measured passes via mass transfer from the bulk solution to the sensor housing to a working electrode where a chemical reaction occurs based on the working electrode surface material and the electrical bias applied to the working electrode with respect to the reference electrode. Electrochemical sensors, such as pH sensors, ion selective sensors, and redox sensors, are equipped with electrical conductors to allow electrical signals to be transmitted to and from electrodes contained within the sensor. An electrochemical sensor used for measuring pH, ORP, or other specific ion concentrations is typically comprised of five parts: an analyte sensing working electrode, a reference electrode, a low work function auxiliary electrode, a temporal electrical potential control source, and an amplifier that translates signal into useable information that can be read. The latter two parts are enabled by the use of an electrochemical controller called a potentiostat. Repeated temporal electrical potentials and measurements make up a pattern that the potentiostat applies to the electrodes to provide the operator with chemically significant results.

Current electrochemical potentiostats have a number of design considerations. Research scientists, laboratories and businesses employing custom electrodes to make analytical measurements as part of their operations need an electrochemical tool as easy to use as an electrochemical meter. An electrochemical meter consists of a potentiostat that automatically recognizes a set of electrodes as a sensor, and a sensor is a set of electrodes that make a specific analyte measurement when operated with predefined electrical potentials. An electrochemical meter is easy to use due to the combination of well defined electrical potentials and electrodes that allow for automatic reporting of the target analyte concentration. Potentiostats employed with a user defined electrode set do not provide for means to recognize the same electrode set in discontinuous experiments. The potentiostat should be inexpensive. Capital equipment costs discourage researchers from performing multiple measurement experiments simultaneously. The potentiostat should have intuitive and relatively simple software. Complex software limits the degree of automation and flexibility that the scientist or engineer can implement. The potentiostat should be able to perform long-term experiments, such as experiments that perform and record measurements over weeks, months and years. The emphasis on data collection speed of most potentiostats has placed significant limits on the ability to perform long-term experiments.

SUMMARY

These and other needs are addressed by the various embodiments and configurations of the present invention. The invention is directed generally to an electrochemical sensor having on board intelligence.

In a first embodiment, a sensor includes:

(a) a plurality of electrode assemblies; and (b) a connector electrically connected to the electrode assemblies, wherein at least one of the following is true:

at least one of the electrode assemblies comprises an electrode memory storing electrode information; and the connector comprises a sensor memory storing sensor information, the sensor information comprising a pattern to be employed by a potentiostat.

Exemplary electrode information includes one or more of an electrode attribute, electrode manufacture time and/or date, electrode manufacturer identifier, manufacturer part number, electrode expiration time and/or date, and a unique electrode identifier.

Exemplary sensor information includes a plurality of a pattern to be employed by the potentiostat to operate at least one of a sensor and electrode assembly, a type identifier of a type of physical data sensed by the sensor, an identifier of the user, a time and/or date of manufacture of the sensor, a time and/or date of first use of the sensor, an expiration time and/or date of the sensor, a maintenance time and/or date to service the sensor, an engineering unit corresponding to the sensor type, an algorithm for data analysis, a unique sensor identifier, and calibration information.

In a second embodiment, a method includes the steps:

(a) determining, by a potentiostat, that at least one of a sensor and electrode is connected to a port;

(b) obtaining, by the potentiostat and from the at least one of a sensor and electrode, a pattern to be employed by the potentiostat to operate the at least one of a sensor and electrode; and (c) performing, by the potentiostat, the pattern.

In a third embodiment, a method includes the steps:

(a) receiving, by a potentiostat and from a user, at least one of a unique identifier, operational sequence, and data processing algorithm; and (b) storing, in memory of at least one of a sensor and electrode, the at least one of a unique identifier, operational sequence, and data processing algorithm.

The present invention can provide a number of advantages depending on the particular configuration. For example, the electrochemical tool can provide a potentiostat/electrode interface that, when interrogated by the potentiostat, can automatically activate measurement readings based on the stored information about the sensor. The tool can identify electrodes and store programming into a group of electrodes to allow accurate replication of an experiment using any potentiostat. The tool can be manufactured at a low capital cost and encourage performance of multiple experiments simultaneously while taking advantage of the multi-channel capabilities and electrical isolation—electrode isolation may be performed using galvanic and/or optical isolation. The tool can include intuitive software to simplify automating multiple experiment types. The software can be designed for long-term automation and make the data retrieval and post processing intuitive and long-term research attractive while preserving short time-scale pattern operations. By keeping the costs low and limiting the features to those which will satisfy ~80% of the common functional capabilities, the conventional paradigm of potentiostats being expensive research tools can be broken, and potentiostats can become a tool as easy to use as a meter. While there are many commercial potentiostats on the market that vary in size, number of channels, electrochemical features and price, none of the current potentiostats on the market utilize smart electrodes or smart sensors. The use of smart electrodes can improve and automate experimental documentation and accountability of the electrodes (as is done with columns placed in high performance liquid chromatographs) and simplify the ease of replicating experiments using different potentiostats and among different laboratories. In fact, combinations of electrodes can be configured as a smart sensor, where all of the necessary electrodes are bundled together and enable the execution of immediate experiments/results without requiring any additional electrodes to be added to the potentiostat or any additional input from the user—meter functionality.

These and other advantages will be apparent from the disclosure of the invention(s) contained herein.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "computer-readable medium" as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, memory card, EPROM, flash, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the invention is considered to include a tangible storage medium or distribution medium and prior art-recognized equivalents and successor media, in which the software implementations of the present invention are stored.

The term "connector" refers to electronics and connectivity to one or more electrodes and normally is part of a sensor.

The terms "determine", "calculate" and "compute," and variations thereof, as used herein, are used interchangeably and include any type of methodology, process, mathematical operation or technique.

The term "electrode" refers to electrochemically active materials of specific geometries and with or without related interfaces to the environment to be measured.

The term "module" as used herein refers to any known or later developed hardware, software, firmware, artificial intelligence, fuzzy logic, or combination of hardware and software that is capable of performing the functionality associated with that element. Also, while the invention is described in terms of exemplary embodiments, it should be appreciated that individual aspects of the invention can be separately claimed.

The term "potentiostat" refers to electronics that provide power and logic, and optionally digital-to-analog conversion, to energize one or more electrodes, optionally analog-to-digital conversion to store the resulting signals, and optionally interfaces with logic to allow the user to design the operating sequence (pattern).

The term "pattern" refers to a temporal operation of analog-to-digital and digital-to-analog operations that provide chemically significant signals to the operator.

The term "sensor" refers to a set of multiple electrodes that, when operated using a specific pattern, provide a relevant signal, commonly without the need for the operator to perform further input or data reduction.

The preceding is a simplified summary of the invention to provide an understanding of some aspects of the invention. This summary is neither an extensive nor exhaustive overview of the invention and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible utilizing, alone or in combination, one or more of the features set forth above or described in detail below.

DETAILED DESCRIPTION

System Overview

Figure 1:
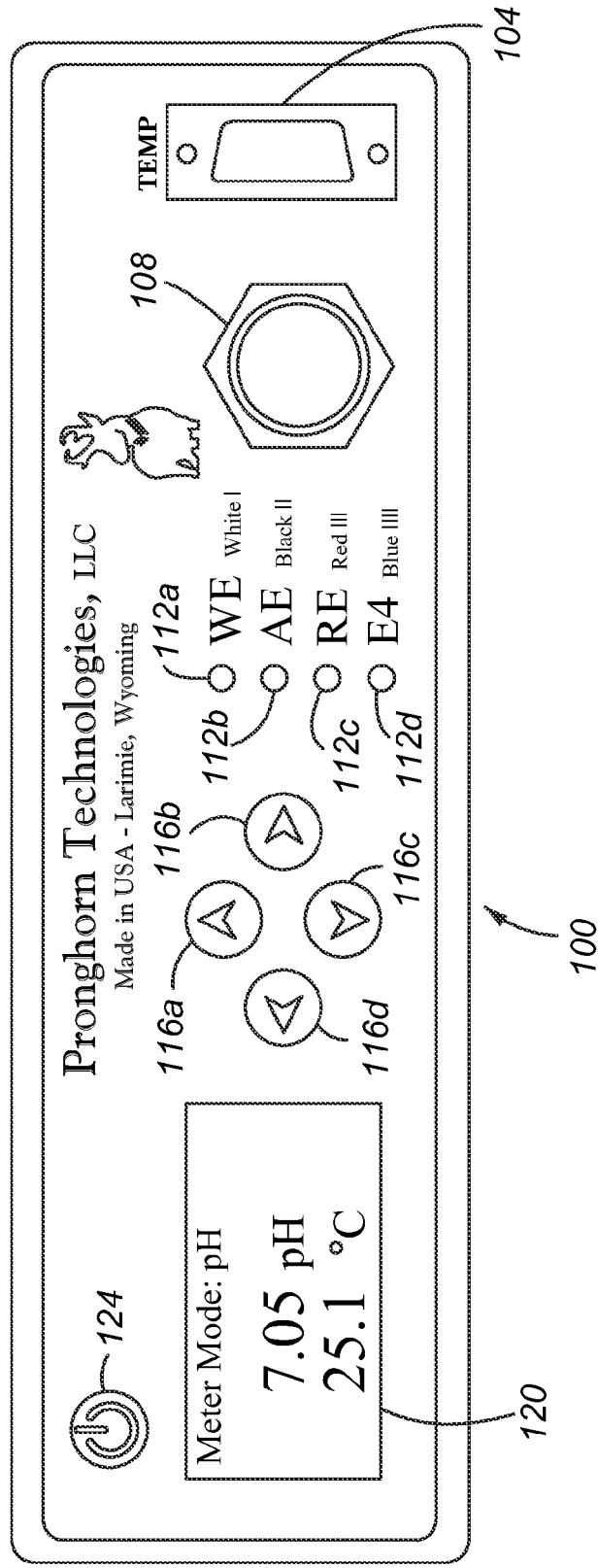
FIG. 1 depicts a user interface portion of a potentiostat according to an embodiment.
Figure 2:
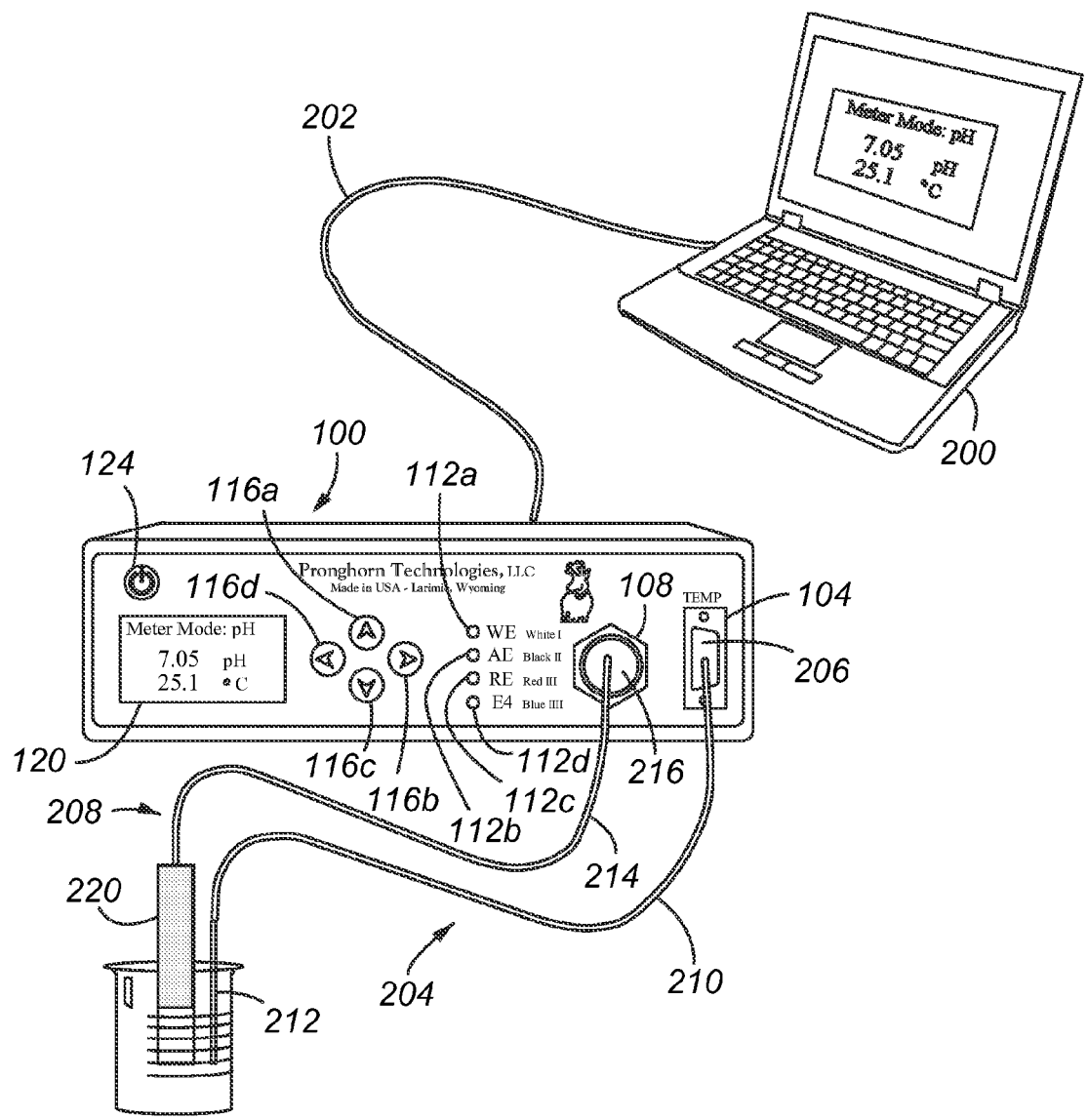
FIG. 2 depicts the potentiostat, in a meter mode, operatively connected with a computer and a sensor.
Figure 3:
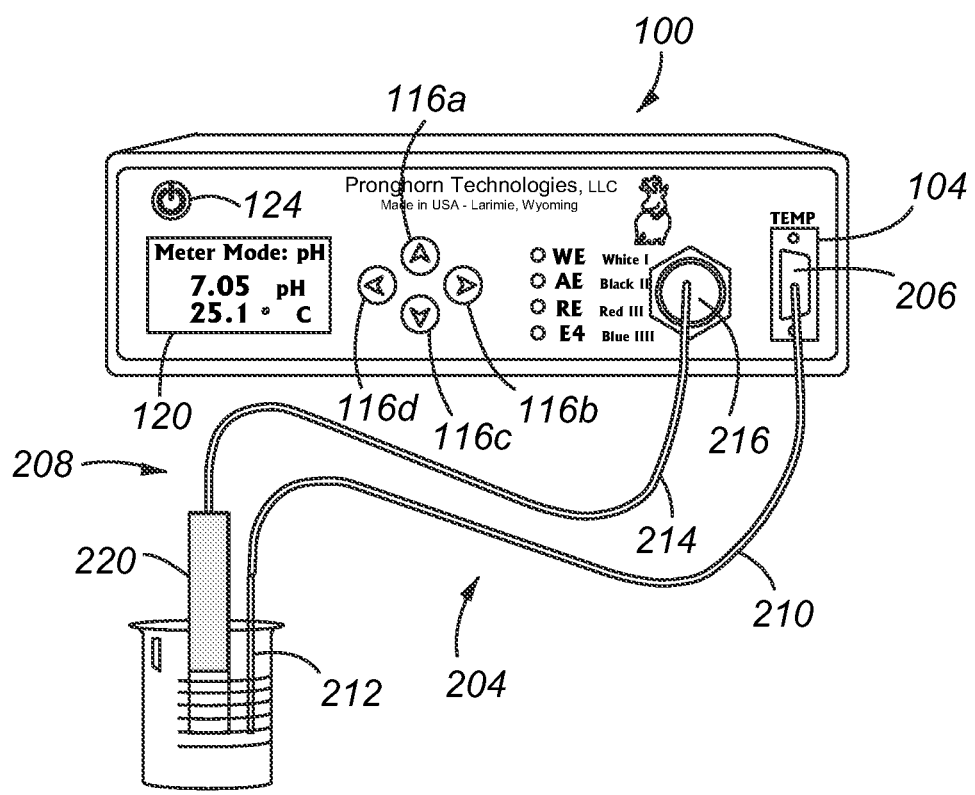
FIG. 3 depicts the potentiostat, in a meter mode, in a stand alone configuration operatively connected with a sensor assembly.
Figure 4:
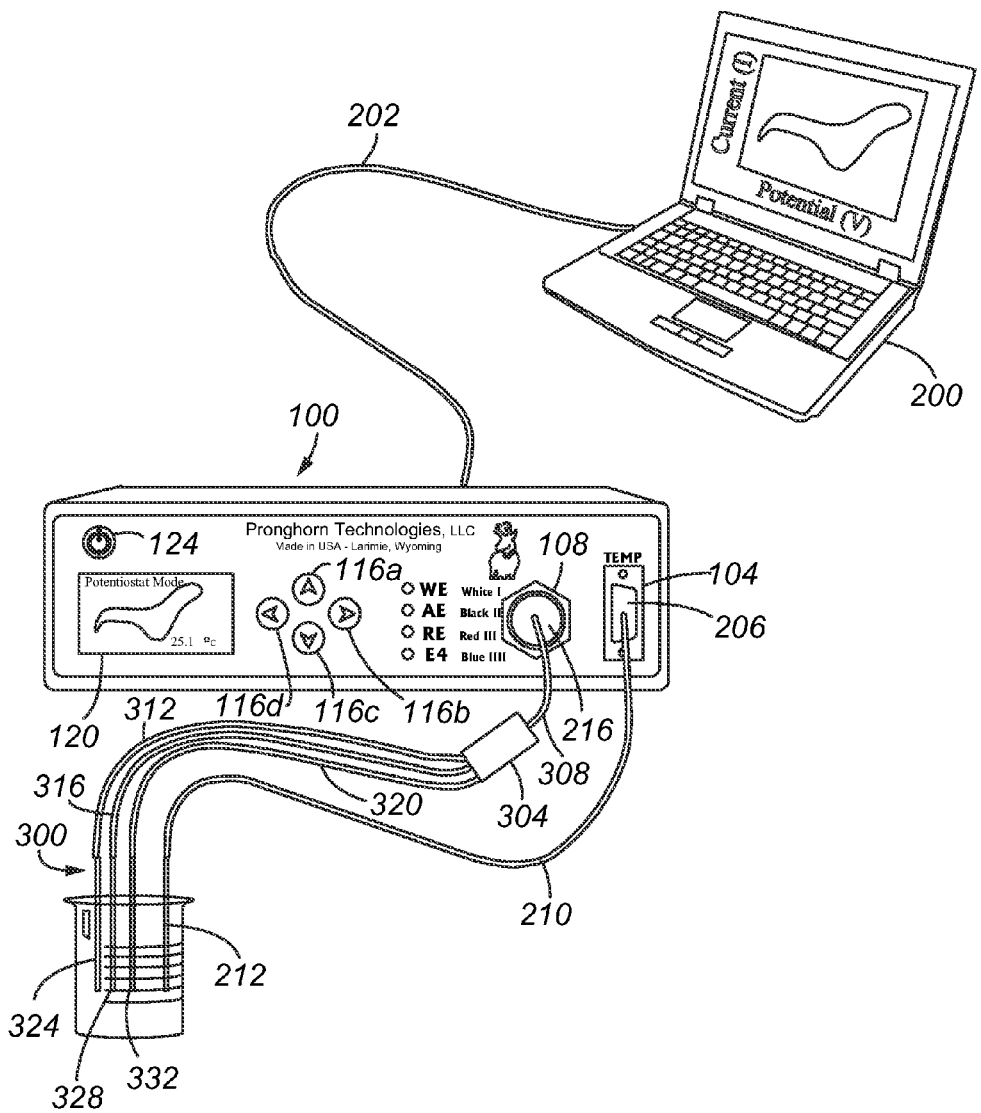
FIG. 4 depicts the potentiostat, in a potentiostat mode, operatively connected with a computer and a sensor.

Embodiments of the disclosure are directed to a combination of a potentiostat and smart, or artificially intelligent, electrode/sensor assembly. The intelligence is provided at two levels. The first level of intelligence, or community intelligence, exists at the sensor layer. At the sensor layer, a microprocessor and/or processor readable and accessible memory is/are provided. The first level intelligence consists of both user programmable and non-programmable sensor attributes. The programmable attributes include predetermined or user configured patterns or methods for operating the sensor. At the second level of intelligence, or electrode intelligence, intelligence exists at the electrode layer. At the electrode layer, a microprocessor and/or processor readable and accessible memory, preferably different from that at the first level, is/are provided. The second level intelligence includes individual electrode attributes and is usually not programmable by the user but is pre-programmed by the electrode manufacturer. The separate levels of intelligence can automate experimental documentation and accountability of the electrodes and simplify the ease of replicating experiments among different potentiostats and among different laboratories.

The System

The potentiostat is generally the user programmable or nonprogrammable electronics that actually generate at selected times and frequencies (e.g., the method or pattern) the electrical potentials or voltages, pulses, and signals that electrically energize selected electrodes, provide the standard voltages, and receive, from the selected electrodes at selected times and frequencies, resulting or responsive electrochemical signal readings. The measurement signals are converted into digital values for later storage or display to the user via a graphical user interface. The potentiostat measurements generally fall into two categories, potentiometric measurements (e.g. voltage galvanometry) and amperometric measurements (e.g. cyclic voltammetry).

A configuration of a user interface of a potentiostat 100 is depicted in FIGS. 1-6. The potentiostat 100 includes a temperature port 104, a sensor port 108, electrode status indicators 112a-d, user tactile selectors 116a-d, graphical display 120, and power switch 124. An external power port and communication (which can be any suitable port such as a USB, parallel or serial) port (to a computer 200 or peripheral device by communication cable 202) (not shown) are also provided. While the temperature port 104 is shown in a serial configuration, it is to be understood that any other port configuration may be employed (such as a parallel port configuration). The sensor port 108 can have any configuration, depending on the application. The temperature port is connected to a temperature sensor 204 (the temperature sensor may be a platinum RTD, thermocouple, or other sensor for providing a signal proportional to the temperature), and the sensor port 108 to a sensor 208. The temperature sensor 204 includes a connector 206 engaging a conductor 210 and a temperature sensor housing 212. The sensor 208 includes a connector 216 engaging the port 108 and a conductor 214, and an electrode housing 220 containing the electrodes (not shown). The sensor 208 may incorporate a means for temperature measurement in conjunction with or in place of a separate temperature sensor 204.

The indicators 112a-d correspond to four electrode configurations, namely a working electrode ("WE"), an auxiliary electrode ("AE"), a reference electrode ("RE"), and fourth electrode ("E4"). The fourth electrode is a "floating electrode" and, depending on the application and user selections received via the selectors 116a-d or the attached computer 200, can take the role any of the other three electrodes, namely working electrode, auxiliary electrode, or reference electrode. In one configuration, the fourth electrode replaces the working electrode, such as to provide parallel measurements. That is, the working electrode and fourth electrode would be used alternatively and sequentially as the working electrode to provide parallel measurements. In another configuration, the fourth electrode is used in addition to the working electrode to expand the surface area of the working electrode. In another configuration, the fourth electrode replaces the auxiliary electrode. In yet another configuration, the fourth electrode is used in addition to the auxiliary electrode to expand the surface area of the auxiliary electrode. Other configurations are possible. Commonly, the indicators are light emitting diodes that indicate, by an illumination or unilluminated state, which of the electrodes is operational or in use. In one configuration, the indicators are not illuminated when the sensor is in use as the user does not need to know more than the sensor reading. Adjacent to each of WE, AE, RE, and E4 is a code indicating the proper connectivity for of the respective electrode (e.g., for WE the code is white (wire) I (one), for AE the code is black (wire) II (two), for RE the code is red (wire) III (three), and for E4 the code is blue (wire) IIII (four)). The Roman numbers represent the number of bands on each wire and are for color blind users.

Figure 5:
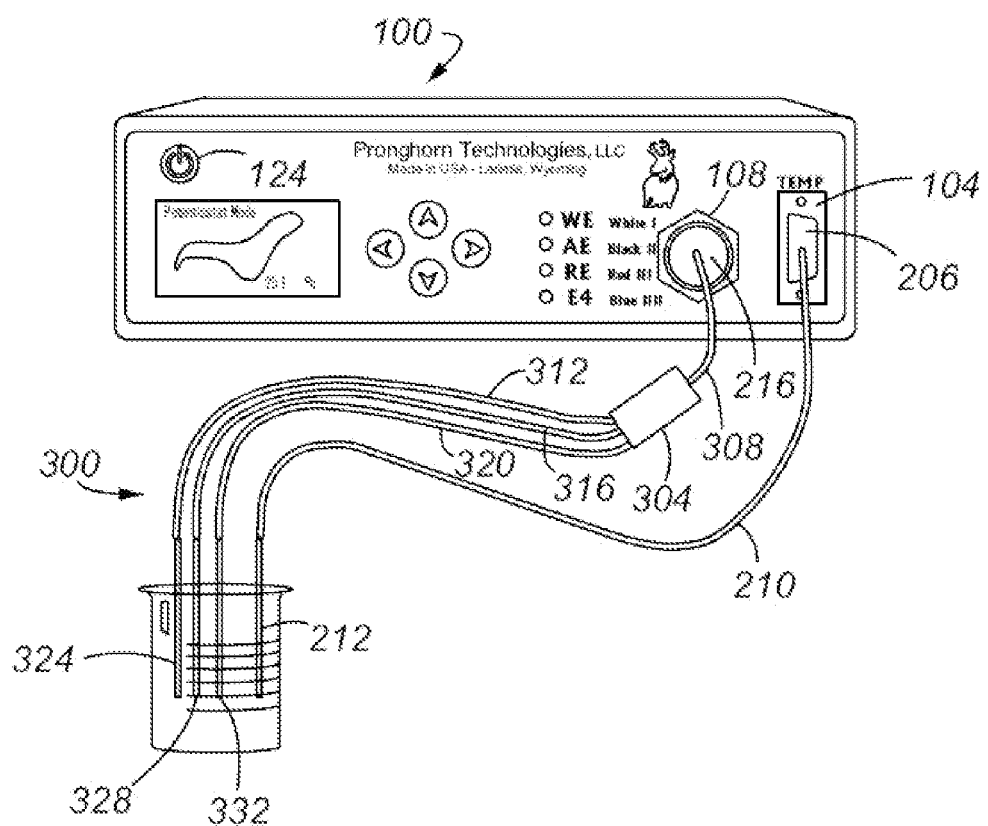
FIG. 5 depicts the potentiostat, in a potentiostat mode, in a stand alone configuration operatively connected with a sensor assembly.
Figure 6:
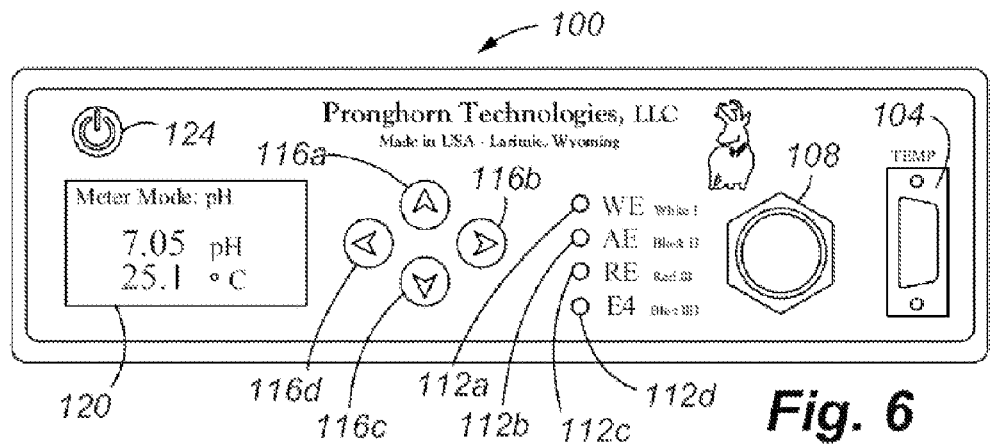
FIG. 6 depicts a user interface portion of a potentiostat according to an embodiment.

The LCD display 120 provides the user with information depending on the particular operating mode of the potentiostat. In the meter mode shown in FIGS. 1-3, the sensor is conventional or standard and the display 120 provides the type of reading (shown as pH) and the measurements, namely the measured pH (shown as pH 7.05) and the temperature as measured by the temperature sensor 204 (shown as 25.1° C.). The potentiostat, in the meter mode, is not controlled by the external computer 200 but is in stand alone operation. In the potentiostat mode shown in FIG. 4, the potentiostat 100 is under the control of the external computer 200 and is typically connected to a nonstandard sensor 300 configured in customized configuration by the user. In FIG. 5, the potentiostat 100 is in the potentiostat mode and is connected to the nonstandard sensor 300. The nonstandard sensor 300 includes the connector 216, a housing 304, a first conductor 308 interconnecting the connector 216 and community electrode connector 304, and second, third, and fourth conductors 312, 316, and 320 connected to second, third and fourth electrodes 324, 328, and 332, respectively.

Figure 7:
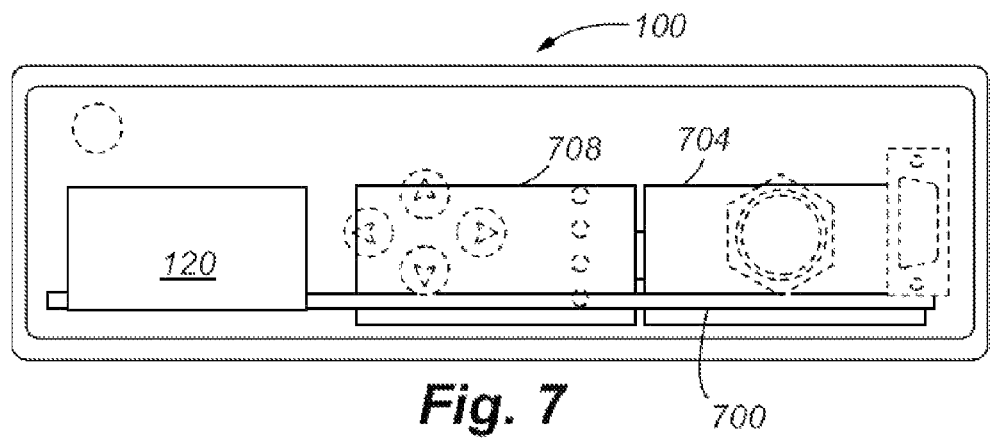
FIG. 7 is a cut-away view of the potentiostat according to an embodiment.
Figure 8:
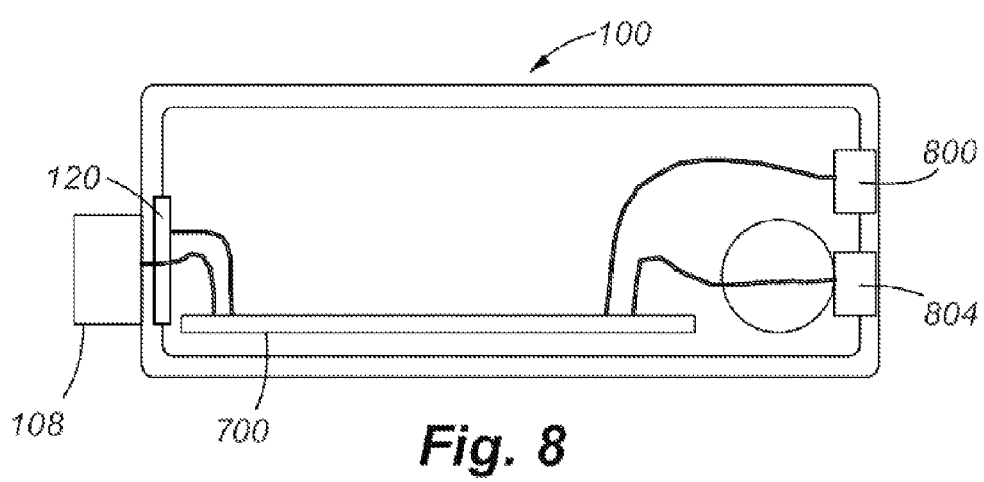
FIG. 8 is a cut-away view of the potentiostat according to an embodiment.

FIGS. 7-8 depict the interior of the potentiostat 100. Referring to FIG. 7, the potentiostat 100 includes a printed circuit board 700, the display 120, and batteries 704 and 708 to provide on board power. Referring to FIG. 8, the potentiostat 100 includes the sensor port 108, and display 120 electrically connected to one end of the circuit board 700, and the external power port 804 and communication port 800 electrically connected to the other end of the board 700.

Figure 9:
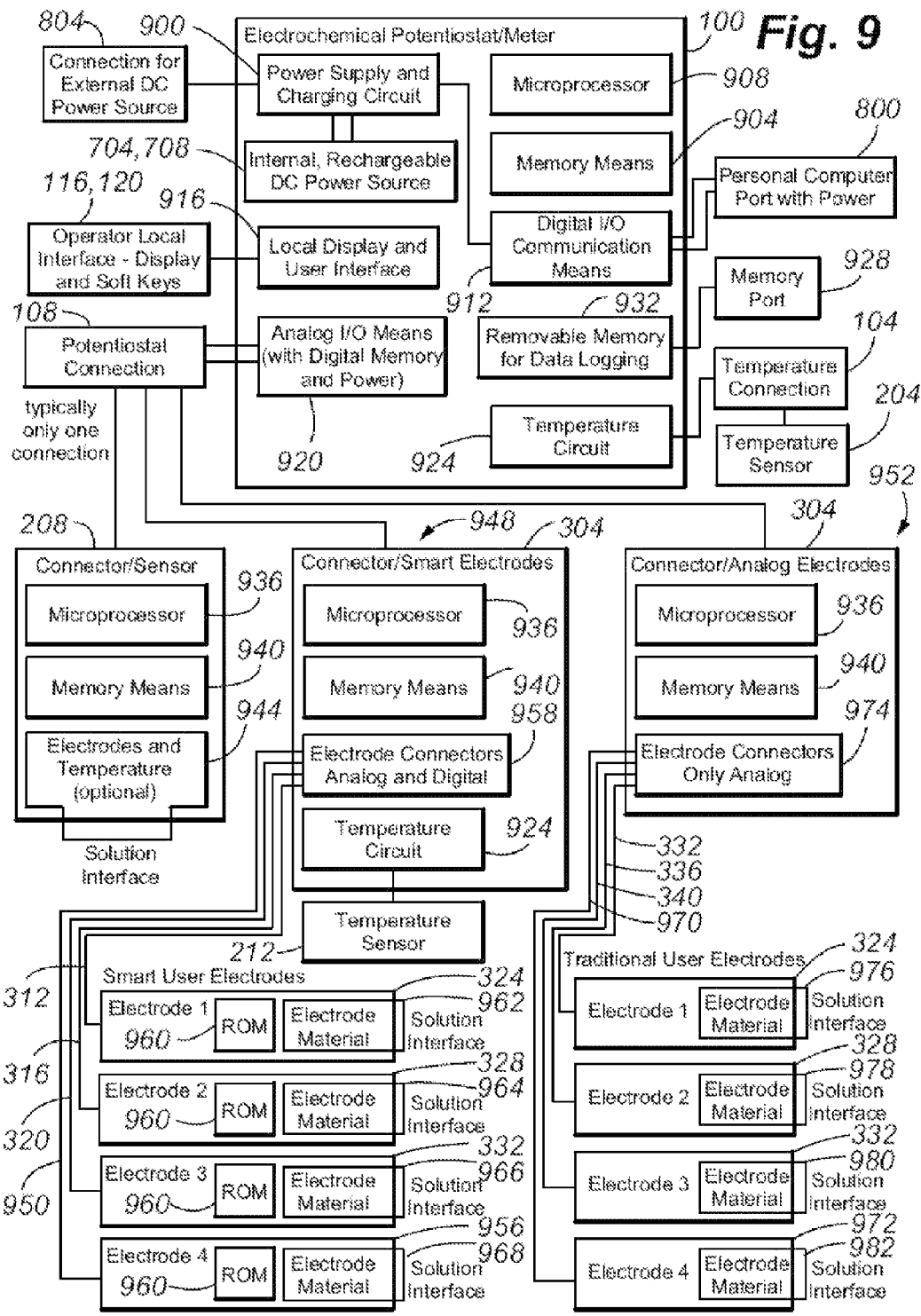
FIG. 9 is a block diagram of a potentiostat and sensor assembly according to an embodiment.

FIG. 9 depicts the functional components of the potentiostat 100 and various sensor configurations. Although typically only one sensor connection is provided by the potentiostat 100, multiple sensors and connections are anticipated by FIG. 9.

The potentiostat 100 includes, on the printed circuit board 700, a power supply and charging circuit 900 to power the board 700, a processor readable memory means 904 to store processor executable instructions and other data, including collected measurements, a microprocessor 908 to execute stored instructions and access the other data, digital input/output communication means 912 to control the transfer of and buffer computer input and output, local display and user interface module 916 to control the keyboard 116 and display 120, analog input/output means 920 with a digital memory to control transfer of and buffer sensor input and output, and a temperature circuit 924 to process signals from the temperature sensor 204. The potentiostat 100 further includes a memory port 928 to include external or removable (secondary) memory 932 for data logging. The power supply and charging and temperature circuits 900 and 924 are conventional. The microprocessor 908 can be any arithmetic and/or logic unit. The local display and user interface module 916 includes device drivers and programmable graphic display. The memory 904 can be any suitable form or type of volatile and/or nonvolatile memory, which includes read only memory ("ROM") and/or random access memory ("RAM"). Typically, the nonvolatile memory 904 will include one or more of mask ROM, PROM, EPROM, EEPROM, and flash memory. The digital input/output communication means 912 and analog input/output means 920 include clock signals and buffers. The potentiostat 100 can include other components, such as a chronometer (not shown) to provide a time and date, a system clock (not shown) to provide timing information, an analog-to-digital converter (not shown), digital-to-analog converter (not shown), a multiplexer/demultiplexer (not shown) simultaneously to transmit signals to and receive signals from multiple electrodes, and the like.

The standard sensor 208 includes the connector 216, a microprocessor 936, a memory means 940, and electrodes 944. The memory means 940 can include a type identifier of a type of physical data sensed by the sensor (e.g., pH, alkalinity, oxidation-reduction potential, dissolved oxygen concentration, and the like), an identifier of the user, a time and/or date of manufacture of the sensor, a time and/or date of first use of the sensor, an expiration time and/or date of the sensor, a maintenance time and/or date to service (e.g., recalibrate) the sensor, a corresponding engineering unit, an algorithm for data analysis (e.g., a scaling factor to be applied to the sensed signals), a unique sensor identifier (such as a serial number), calibration information, a pattern or method operational sequence (pattern) for the electrodes (e.g., pre-conditioning, operation, data collection, and post-conditioning) to be employed by the potentiostat 100, and actual or example test results or measurements. As will be appreciated, there are normally two classes of sensed signals. The first class is representative of a sensed physical parameter that is a function of time; the second class is representative of sensed physical data that is not a function of time. For either class of sensed signal, the sensed signal is an electrical impulse (e.g., voltage, resistance, or current).

The smart electrode set 948 includes the connector 304, signal conductors 312, 316, 320, and 950 and corresponding electrodes 324, 328, 332, and 956. The connector 304 houses a microprocessor 936, memory means 940, electrode connectors 958 for analog and digital electrodes, and a temperature circuit 924 for the temperature sensor 212. The memory means 940 can include the same processor readable information as the memory means 940 in the sensor 208. Each electrode further includes ROM 960 and a suitable electrode material 962, 964, 966, and 968 for interacting with a fluid to be measured. The ROM 960 includes processor readable information including electrode material type, and electrode material shape and/or dimensions (e.g., length, width, thickness, surface geometry (e.g., planar, circular, elliptical, star shaped, rectangular, coiled, microarray, etc.)), electrode manufacture time and/or date, electrode manufacturer identifier, manufacturer part number, electrode expiration time and/or date, and/or a unique electrode identifier. Suitable electrode materials, for example, include platinum, silver, gold, graphite, silver chloride, silver bromide, and glassy carbon. The stored information can be used by the potentiostat or computer to identify potential configuration conflicts or defects and alarm and/or direct the user to resolve the conflict or defect. As will be appreciated, the digital signals are handled in separate electrical lines from the analog signals.

In one configuration, the microprocessor, at either the sensor or electrode layer, determines that an expiration time and/or date has expired. In response, the microprocessor deactivates the sensor or electrode, as appropriate. This prevents the sensor or electrode from being used too long and producing less accurate measurements. As will be appreciated, the performance of many electrodes and/or sensors deteriorates over time. The user could be provided, via the display, with a remaining useful life of the sensor or electrode. The remaining useful life may be provided in absolute or relative terms.

In one configuration, the microprocessor, at the sensor layer, determines that a maintenance time and/or date has expired. In response, the microprocessor deactivates the sensor. When the sensor is serviced (e.g., recalibrated), it is reactivated by the microprocessor. This prevents the sensor from producing inaccurate measurements by ensuring periodic recalibration. The user could be provided, via the display, with a time and/or date to service the sensor. As will be appreciated, there are no recalibrations for individual electrodes and therefore the ROM 960 need not have provisions for writing information from the user.

The analog electrode set 952 includes the connector 304, signal conductors 332, 336, 340, and 970 and corresponding electrodes 324, 328, 332, and 972. The connector 304 houses a microprocessor 936, memory means 940, and electrode connectors 974 for analog only electrodes. The memory means 940 can include the same processor readable information as the memory means 940 in the sensor 208. Since this electrode connector 304 is designed to be compatible with traditional electrochemical electrodes, the ROM 960 components of the smart electrodes are not present and therefore not electrically connectable in the 304 connector for the 952 electrode set. The electrode materials 976, 978, 980, and 982 for interacting with a fluid to be measured may be of any type from any manufacturer and may be of any age and condition. As will be appreciated, analog signals are preferably passed from the electrode materials through the connections to the potentiostat with virtually no stray impedance or break in conductor shielding.

As shown in FIG. 9, there are four different sensor types that can mate with the potentiostat sensor port 108.

A first type of sensor, an example of which is sensor 208, is an electrode set comprising multiple, smart, preconfigured electrodes. These electrodes, in-effect, enable the meter mode functionality via the use of an embedded memory chip or a low-cost microprocessor. The embedded microprocessor contains the operational sequence (pattern) for the electrodes, such as pre-conditioning, operation, data collection, and post-conditioning. Engagement of a connector of one of these pre-programmed meter sensors with the sensor port 108 immediately activates the potentiostat 100 and prompts the user to the experiment type and other user steps that need to be manually accomplished to assure accurate experiment execution. No potentiostat made to date has the ability for the sensor to contain experimental steps and prompt the user as well as store both the calibration information and algorithms for data analysis. This sensor configuration enables a meter mode functionality defined by the manufacturer. Sensors will be programmed with a shelf and operational life. The sensor can be disabled after expiration of a predetermined sensor operational life as determined by the date stamp maintained in the first level of intelligence. The various connector pins in the connector 108 include a pin for the working electrode ("WE"), a pin for WE ground ("GND"), a pin for the auxiliary electrode ("AE"), a pin for the reference electrode ("RE"), a pin for the RE shield, a pin for the electrode 4 ("E4"), and three pins to accommodate digital communication with the microprocessor 936 and memory means 940 with a pin for the digital signal, a pin for power, and a pin for common, representative of SPI communications.

The first type of sensor has a special file on a root directory. When the sensor is connected to the port 108 or the potentiostat activated, the potentiostat initiates an automatic execute command. The potentiostat uploads automatically and executes the method from the memory means 940.

A second type of sensor, an example of which is sensor 948, is an electrode set comprising multiple, smart, user configured (user programmable) electrodes making custom sensors. These electrodes allow the user to attach individual selected electrodes and program the electrode set with a unique identification, operational sequence (method or pattern), and the data reduction or processing algorithm(s). Such programming into the unique electrode interface 304 can allow the laboratory manager or researcher to replicate experiments at many sites that may employ different potentiostats with the proper electrodes. In traditional laboratory settings, neither the electrodes nor the condition of the electrode are readily identified. The electrode interface 304 allows the user to retrieve easily the electrode identification in addition to the method for using the electrodes. This operational mode is user-defined meter functionality. A user is inclined to have several of these connectors per potentiostat. The connector 304 will only interface with smart, self-identifying electrodes, that are manufactured for the potentiostat 100. Once the interface or connector 304 is programmed the electrode set becomes a sensor that can be distributed and used to replicate the experimental results with a low potential for error. The various connector pins in the connector 304 include a pin for the WE, a pin for the WE GND, a pin for the AE; a pin for the RE, a pin for the RE shield, a pin for the E4; a pin for the digital signal to read the microprocessor signals and the electrode ROM's, a pin for power, and finally a pin for common. The user leads include at least a four-wire WE connector, AE connector, RE connector, and E4 connector.

Programming of the sensor is done using the computer 200. The user commands are forwarded to the potentiostat for storage and/or downloaded to the sensor memory means 940 for storage.

A third type of sensor, an example of which is sensor 948, is an electrode set comprising smart electrodes having no user programmability. These electrodes allow the use of "smart" electrodes that are identified by the potentiostat but do not have previously programmed user programming with respect to an operational sequence (pattern) or data reduction algorithm. This mode of operation, and the second level of intelligence, allow the user to verify that the attached electrodes are as expected (material, dimensions, and conditioning). The electrode identification information will be automatically stored with any saved experimental data on the computer 200. This operational mode is enhanced potentiostat functionality where the electrodes are identified and improves electrochemical method documentation and reduces documentation errors. A user is inclined to have one of these connectors per potentiostat. The connector 304 will only interface with smart, self-identifying electrodes, that are manufactured for this potentiostat 100. The various connector pins in the connector 304 include a pin for the WE, a pin for the WE GND, a pin for the AE, a pin for the RE, a pin for the RE shield, a pin for the electrode 4 (E4), a pin for the digital signal to read the microprocessor and the electrode ROM's, a pin for power, and a pin for common. The user leads include at least a four-wire WE connector, AE connector, RE connector, and E4 connector.

A fourth type of sensor, an example of which is sensor 952, is an electrode set comprising a smart override interface connector 304. This connector informs the potentiostat the there is no automated electrode identification ROM 960 information. There may or may not be previously stored information related to an operational sequence (pattern) or data reduction algorithm. The potentiostat is thus operated in a mode similar to that found in traditional potentiostats where the user must take responsibility for the affixed electrodes and the way the electrodes are operated. This operational mode is an enhanced traditional potentiostat functionality where the electrodes are not identified but pattern and data reduction information may be stored to improve experiment reproduction. A user is inclined to have one of these connectors per potentiostat traditional operation but may have more if custom non-smart electrode sensors are created. The potentiostat may be used with any electrochemical electrode on the market from any source. The various connector pins in the connector 304 include a pin for the WE, a pin for the WE GND, a pin for the AE; a pin for the RE, a pin for the RE shield, a pin for the E4; a pin for the digital signal from the microprocessor, a pin for power, and finally a pin for common. The user leads include a one-wire/clip for the WE connector, AE connector, RE connector, and E4 connector.

In one alternative embodiment, the potentiostat is modified to include multiple ports. One port is port 108 for smart electrodes. Other ports are for individual connectors for each electrode. The latter ports are for the standard WE, AE, RE, and E4 electrodes. In the latter configuration, there may be intelligence at both the electrode connector and electrode layers.

System Operation

Figure 10:
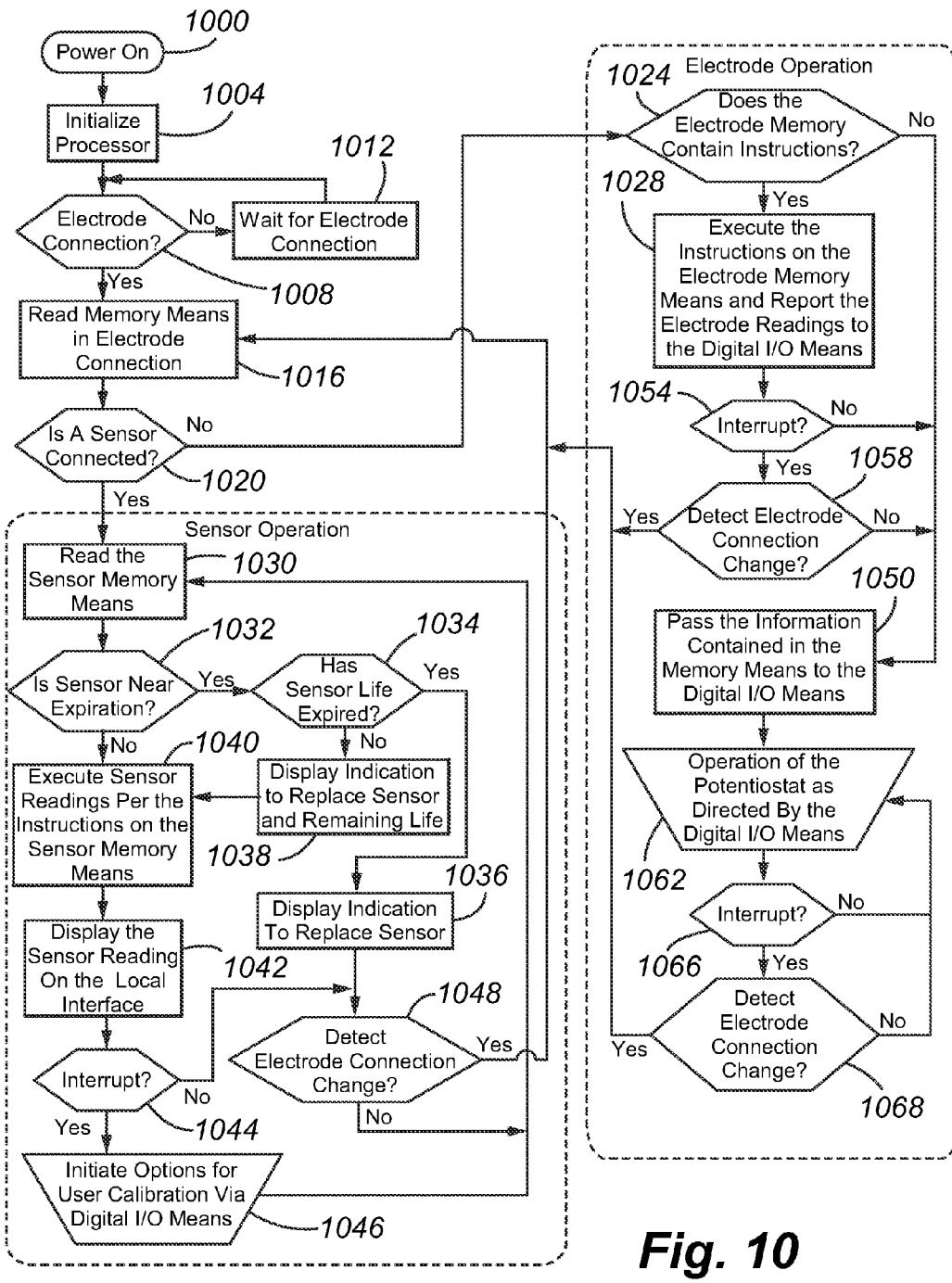
FIG. 10 is a flow chart of the operation of a potentiostat according to an embodiment.

FIG. 10 depicts an operation embodiment of the potentiostat.

In step 1000, the potentiostat is activated by the user, and, in step 1004, the potentiostat processor initialized.

In decision diamond 1008, the processor determines whether an electrode is connected directly to a potentiostat port. If not, the processor, in step 1012 awaits electrode connection. If so, the processor in step 1016 reads stored information from the memory means 940 of the selected electrode. This loop is repeated until the memory means of each electrode is accessed.

In decision diamond 1020, the processor determines whether or not a sensor is connected to a potentiostat port 108. When a sensor is not connected to a port, the processor proceeds to decision diamond 1024 (discussed below) only with the information retrieved from the electrode memory means 940. When a sensor is connected to a port, the processor, in step 1030, reads the information stored in the sensor memory means 940.

In decision diamond 1032, the processor determines, based on the sensor expiration time and/or date, whether or not the sensor is near expiration. When the sensor life is near expiration, the processor, in decision diamond 1034, determines whether or not the sensor life has expired. When the sensor life has expired, the processor, in step 1036, displays an indication to replace the sensor. When the sensor life has not expired, the processor, in step 1038, displays an indication to replace the sensor along with the sensor's remaining life.

When the sensor life is not near expiration or after step 1038, the processor, in step 1040, executes the sensor readings per the instructions on the sensor memory means 940. Control then passes to step 1042.

In step 1042, the potentiostat processor displays the sensor readings on the display 120.

In decision diamond 1044, the processor determines whether or not it has received an interrupt. If so, the processor, in step 1046, initiates options for user calibration via the digital input/output communication means 912 and returns to step 1030. If not or after step 1036, the processor proceeds to decision diamond 1048. An interrupt may be in the form of, but not limited to, the disconnection of the sensor from port 108, connection of a different sensor to port 108, or software communication from a computer 200 using communications port 800.

In decision diamond 1048, the processor determines whether it has detected an electrode connection change. When a change is detected, the processor returns to step 1016. When a change is not detected, the processor proceeds to step 1030.

Returning to decision diamond 1024, the processor determines whether or not the electrode memory means 940 contains instructions. When the electrode memory means 940 contains instructions, the processor, in step 1028, executes the instructions on the electrode memory means and reports the electrode readings to the digital input/output communication means 912. When the electrode memory means does not contain instructions, the processor proceeds to step 1050 (discussed below).

After step 1028, the processor determines, in decision diamond 1054, whether or not an interrupt has been received. When an interrupt is not received, the processor proceeds to step 1050 (discussed below). When an interrupt is received, the processor determines in decision diamond 1058 whether an electrode connection change has occurred. When an electrode connection change occurs, the processor returns to step 1016. When no electrode connection change has occurred, the processor proceeds to step 1050.

In step 1050, the processor passes the information contained in the memory means to the digital input/output communication means 912.

In step 1062, the processor operates the potentiostat as directed by input received by the digital input/output communication means 912.

In decision diamond 1066, the processor determines whether or not an interrupt has been received. If not, the processor returns to step 1062. If so, the processor determines, in decision diamond 1068, whether an electrode connection change has been detected. If not, the processor returns to step 1062. If so, the processor returns to step 1016.

In one configuration, the potentiostat maps the current electrode connections against connections for the sensor type. Defects are brought to the attention of the user and, in some applications, instructions provided by the display 120 or computer 200 to correct the defect.

The exemplary systems and methods of this invention have been described in relation to a potentiostat and local sensor and computer. However, to avoid unnecessarily obscuring the present invention, the preceding description omits a number of known structures and devices. This omission is not to be construed as a limitation of the scope of the claimed invention. Specific details are set forth to provide an understanding of the present invention. It should however be appreciated that the present invention may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as a portable or nonportable potentiostat, or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the invention.

A number of variations and modifications of the invention can be used. It would be possible to provide for some features of the invention without providing others.

For example the sensor can operate in multiple modes, each mode corresponding to a different type of measurement. In this embodiment, the first level of intelligence would include different information for each mode and a mode (or sensor type) identifier. For example, a first sensor type would include first calibration information, first method or pattern, first scaling factor, first engineering unit, and the like and a second sensor type would include second calibration information, second method or pattern, second scaling factor, second engineering unit, and the like. The user can select a particular operating mode for the sensor by selecting a proper mode identifier from among a stored plurality of mode identifiers.

In another embodiment, multiple connectors can be stacked one-on-top of the other using a common port 108. The user could, using the keypad or external computer, select a particular sensor to operate or receive data from at a particular time. The selection could be effected using a unique identifier of the sensor or a sensor type identifier (assuming that different types of sensors are in the stack). The simultaneous use of multiple sensors with a single microprocessor can create problems in accurate electrochemical readings because of the difficulty in maintaining time scales accurately. As a result the best results may be achieved by using a single sensor per potentiostat 100 and connecting multiple potentiostats to one or more computers 200.

In yet another embodiment, the systems and methods of this invention can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this invention. Exemplary hardware that can be used for the present invention includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this invention is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this invention can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present invention describes components and functions implemented in the embodiments with reference to particular standards and protocols, the invention is not limited to such standards and protocols. Other similar standards and protocols not mentioned herein are in existence and are considered to be included in the present invention. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present invention.

The present invention, in various embodiments, configurations, and aspects, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments, configurations, or aspects for the purpose of streamlining the disclosure. The features of the embodiments, configurations, or aspects of the invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the invention.

Moreover, though the description of the invention has included description of one or more embodiments, configurations, or aspects and certain variations and modifications, other variations, combinations, and modifications are within the scope of the invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A measuring system, comprising:
   a potentiostat;
   a sensor comprising a plurality of electrodes; and
   a connector electrically connected to the electrodes,
   wherein at least one of the plurality of electrodes comprises a memory,
   wherein the connector comprises an operational sequence to be employed by the potentiostat.

2. The measuring system of claim 1, wherein at least one of the plurality of electrodes comprise electrode information comprising one or more of an electrode attribute, electrode manufacture time and/or date, electrode manufacturer identifier, manufacturer part number, electrode expiration time and/or date, and a unique electrode identifier.

3. The measuring system of claim 2, wherein the electrode information differs from the sensor information and wherein the sensor information further comprises a plurality of a type identifier of a type of physical data sensed by the sensor, an identifier of the user, a time and/or date of manufacture of the sensor, a time and/or date of first use of the sensor, an expiration time and/or date of the sensor, a maintenance time and/or date to service the sensor, an engineering unit corresponding to the sensor type, a unique sensor identifier, and calibration information.

4. The measuring system of claim 2, wherein the electrode information comprises an electrode attribute and wherein the electrode attribute is material type, electrode material shape, and/or dimensions.

5. The measuring system of claim 2, wherein the electrode information comprises at least one of an electrode manufacture time and/or date and an electrode expiration time and/or date.

6. The measuring system of claim 2, wherein the electrode information comprises a unique electrode identifier.

7. The measuring system of claim 3, wherein the sensor information comprises at least one of an expiration time and/or date of the sensor, a time and/or date of first use of the sensor, and a maintenance time and/or date to service the sensor.

8. The measuring system of claim 3, wherein at least one of the plurality of electrodes is replaceable.

9. The measuring system of claim 1, wherein the operating sequence is at least one of pre-conditioning, operation, data collection, and post-conditioning.

10. A method, comprising:
    determining, by a potentiostat, that at least one of a sensor and an electrode is connected to a port, the sensor comprising a plurality of electrodes;
    receiving, by the potentiostat, an operational sequence, the operational sequence provided-by a connector, the connector electrically connected to the electrodes, wherein at least one of the plurality of electrodes comprises a memory; and
    performing, by the potentiostat, the operational sequence.

11. The method of claim 10, wherein the operational sequence pattern is programmed into the connector by a user.

12. The method of claim 10, wherein the sensor information comprises a plurality of a type identifier of a type of physical data sensed by the sensor, an identifier of the user, a time and/or date of manufacture of the sensor, a time and/or date of first use of the sensor, an expiration time and/or date of the sensor, a maintenance time and/or date to service the sensor, an engineering unit corresponding to the sensor type, a unique sensor identifier, and calibration information.

13. The method of claim 10, wherein at least one of the plurality of electrodes comprise electrode information comprising one or more of an electrode attribute, electrode manufacture time and/or date, electrode manufacturer identifier, manufacturer part number, electrode expiration time and/or date, and a unique electrode identifier.

14. The method of claim 10, further comprising:
    determining, by the potentiostat, that an operational life of the at least one of a sensor and an electrode has expired; and
    in response, not performing, by the potentiostat, the operational pattern.

15. The method of claim 10, further comprising:
    determining, by the potentiostat, that a service period associated with the at least one of a sensor and an electrode has expired; and
    in response, not performing, by the potentiostat, the operational sequence until predetermined service is performed by a user.

16. The method of claim 10, wherein each of the plurality of electrodes has a respective electrode memory comprising a corresponding unique electrode identifier.

17. A method, comprising:
    receiving, by a potentiostat and from a user, an operational sequence; and
    storing, in a memory of at least one of a sensor and an electrode, the operational sequence, wherein the electrode comprises a memory.

18. The method of claim 17, further comprising receiving, by a potentiostat and from a user, a unique identifier.

19. The method of claim 17, wherein the at least one of a unique identifier and operational sequence is the operational sequence.

20. The method of claim 17, wherein the memory of the at least one of a sensor and an electrode comprises a non-transitory computer readable medium comprising at least one of a unique identifier and the operational sequence.

* * * * *